United States Patent [19]

Partain et al.

[11] 4,257,001
[45] Mar. 17, 1981

[54] RESONANT CIRCUIT SENSOR OF MULTIPLE PROPERTIES OF OBJECTS

[75] Inventors: Larry D. Partain, Pleasanton; Mysore R. Lakshminarayana, Mission Viejo, both of Calif.

[73] Assignees: John G. Abramo; Samuel V. Abramo, both of Wilmington, Del.

[21] Appl. No.: 29,676

[22] Filed: Apr. 13, 1979

[51] Int. Cl.³ .......................................... G01R 27/04
[52] U.S. Cl. .................... 324/58.5 C; 324/58.5 A; 324/61 QS; 324/263
[58] Field of Search ............ 324/58.5 C, 58 C, 58 R, 324/58.5 A, 57 SS, 57 R, 61 QS, 263

[56] References Cited

U.S. PATENT DOCUMENTS

| | | | |
|---|---|---|---|
| 3,437,922 | 4/1969 | Miller, Jr. | 324/58.5 C |
| 3,458,808 | 7/1969 | Agdur | 324/58.5 C |
| 3,586,971 | 2/1969 | Bosisio | 324/58.5 C |
| 3,612,996 | 10/1971 | Bleackley | 324/58.5 A |
| 3,684,952 | 8/1972 | Lundstrom | 324/58.5 A X |
| 3,688,188 | 8/1972 | Bak et al. | 324/58.5 C |
| 3,739,263 | 6/1973 | Henoch | 324/58.5 C |
| 3,927,369 | 12/1975 | Billeter et al. | 324/58.5 C |
| 4,087,738 | 5/1978 | Van Degrift et al. | 324/61 QS |
| 4,087,798 | 5/1978 | Thorn et al. | 324/58.5 C X |
| 4,155,035 | 5/1979 | Fitzky | 324/58.5 C |

Primary Examiner—Stanley T. Krawczewicz
Attorney, Agent, or Firm—Abramo & Abramo

[57] ABSTRACT

The invention is a resonant circuit sensor of physical properties of objects that monitors measurable properties of resonant circuits affected by interactions of the objects with the polarized, resonant oscillations of the circuits. The circuits can be passive with excitation by an external energy source or active with a source included as an integral part. Simultaneous or sequential sensing of more than one physical property of objects is obtained by detecting resonant oscillation characteristics such as amplitude, frequency, phase or polarization and by detecting quantities influenced by such characteristics for one or more orientations of the objects relative to the polarization of the oscillations. These resonant oscillations can be in the form of electromagnetic fields, electric fields, magnetic fields, or acoustic waves. For electromagnetic fields in the microwave frequency range, device structures, such as Gunn device flanges, that have current and voltage properties that depend on microwave signal properties can provide versatile output signals for the sensor. The sensing can be relative and detect differences in object properties and it can be absolute and measure values for object properties.

34 Claims, 27 Drawing Figures

RESONANT CIRCUIT SENSOR OF MULTIPLE PROPERTIES OF OBJECTS

BACKGROUND OF THE INVENTION

In the computer age of mass information processing, a major factor impeding computer applications are the weaknesses of the transducers available to translate the physical properties of objects into electrical signals with minimum disturbance. Transducers are needed that are fast, accurate, simple, reliable, inexpensive, and nondisruptive. Of the myriad techniques that can be used, resonant circuit sensors provide the distinct advantages of eliminating the need for physical contact with the measured objects, of having the potential for high speed, and of being able to simultaneously measure more than one property. Such sensors have been plagued in the past with complexity, instabilities, limited sensitivites, and high cost.

Many resonant circuit sensors are capable of only a single measurement capability, even though their output is sensitive to a variety of properties of often measured objects. This produces drift and stability problems and it becomes confusing as to which parameters are changing. Also such sensors frequently require rather complex, swept frequency, energy sources.

Resonant detectors of multiple parameters have been of two types—noninteractive and interactive. The noninteractive ones have no interactions between the measured substances and the oscillating wave fields of the resonators. Physical contact with the object is then required and a major advantage of resonant techniques is lost. Existing interactive techniques require precise, swept frequency oscillators for a detailed determination of the resonant sensor's response at frequencies on and off resonance in a manner that defines the quality factor or Q of the sensor. This, in turn, can be translated into two separate properties of the measured substances after complex calculations and calibrations for a limited range of measured properties. Accurate and repeatable measurements require sophisticated and experienced operators and elaborate equipment.

The present invention provides a high speed, noncontacting transducer to simultaneously convert physical properties of objects into electrical signals with high accuracy, good stability, relative simplicity, and low cost. It does not require the off resonance excitations needed for swept frequency Q measurements. It should provide increased capabilities for applications as diverse as frozen food processing, sterile manufacture of medical products, and transportation safety aids.

PRIOR ART

The prior art related below concerns microwave resonant circuit sensors. However, the general knowledge of the microwave area is representative of the general state of knowledge in the larger subject of electric, magnetic, laser and acoustic resonant circuit sensors.

Prior microwave resonant circuit sensors in U.S. Pat. Nos. 3,927,369 (1975); 3,739,263 (1973); 3,684,952 (1972); 3,612,996 (1971); 3,586,971 (1971); 3,458,808 (1969); 3,437,922 (1969) have required swept frequency oscillators to determine properties of the resonant circuit such as changes in the resonant frequency. Such resonant frequency sensors require a high Q structure for accurate determination of frequency shifts. Swept frequency operation (as opposed to single frequency operation) is required because of inherent resonant frequency drift of separated microwave sources and microwave cavities. If high enough cavity Q is used for accurate resonant frequency measurement, the uncorrelated drift of source oscillating frequency and cavity resonating frequency result in uncontrolled variations in the output signal. Nevertheless, such single frequency source monitoring of a separate resonant cavity has been described in U.S. Pat. No. 3,612,996 (1971).

Prior microwave resonant circuit sensors of two physical properties, that utilize the well-known techniques of monitoring changes in resonant frequency $\Delta f$ and changes in cavity quality of factor $\Delta Q$, require swept frequency microwave sources and detection equipment for determining amplitude response as a function of swept frequency. Accurate Q determination requires complex signal analysis or calibration. This contrasts to the present invention that can sense more than one physical parameter with just a frequency determining instrument or with just a frequency determining instrument and a dc voltmeter or ammeter.

A prior microwave resonant circuit sensor of multiple parameters in U.S. Pat. No. 3,927,369 (1975) has no interactions between the sensed material and the microwaves. It requires mechanical or thermal contact between the measured material and the resonant circuit.

The following references were also considered as part of the background relating to this invention:

1. M. Sucher and J. Fox, Eds., *Handbook of Microwave Measurements*, New York: Polytechnic Press, 1963.
2. H. B. G. Casimir, "On the Theory of Electromagnetic Waves in Resonant Cavities," Philips Research Reports, Vol. 6, pp. 162–182, 1951.
3. R. A. Waldron, *The Theory of Waveguides and Cavities*, New York: Gordon and Breach Science Publ., 1969.
4. A. J. Baden Fuller, *Microwaves*, 1st Ed., New York: Pergamon Press, 1969.
5. N. Marcuvitz, Ed., *Waveguide Handbook*, M.I.T. Radiation Laboratory Series, Vol. 10, New York: McGraw-Hill, 1951.
6. H. R. L. Lamont, *Waveguides*, 3rd Ed., New York: John Wiley and Sons, 1950.
7. J. Bybokas and B. Farrell, "The Gunn Flange—A Building Block for Low-Cost Microwave Oscillators," Electronics, Vol. 44, pp. 47–50, Mar. 1, 1971.
8. T. P. Lee and R. D. Standley, "Frequency Modulation of a Millimeter—Wave IMPATT Diode Oscillator and Related Harmonic Generation Effects," Bell System Tech. J., Vol. 48, pp. 143–161, January 1969.
9. W. M. Sharpless, "Wafer-Type Millimeter Wave Rectifiers," Bell System Tech. J., Vol. 35, pp. 1385–1402, Nov. 1956.

In the following specification, numbers in brackets refer specifically to one of the numbered references above. This indicates that additional information on the subject matter directly preceding the brackets is contained in the indicated reference.

SUMMARY OF THE INVENTION

The invention is a high speed, non-contacting transducer to simultaneously determine the physical properties of objects by measurement of electrical signals that are responsive to the properties of the resonant circuit oscillations that are affected by the objects. These transducers provide high accuracy, good stability, relative simplicity, and low cost. The applications for the invention include subject matter as diverse as frozen food processing, sterile manufacture of medical products, and transportation safety aids. These objectives are obtained by devices of this invention which provide for:

1. The measurement of a plurality of physical properties of an object regardless of the method by which the resonant structure means is energized at its resonant frequencies, which involves:
   (a) placing an object relative to the polarization of the resonant oscillations of the resonant structure means so that the oscillations of said structure is perturbed.
   (b) measuring the difference between the characteristics of the perturbed and unperturbed resonant oscillations of the resonant structure.

2. A method for measuring a plurality of physical properties of an object in which the resonant structure means is energized by an energy source only at frequencies at which the structure is resonant, detection of the differences between perturbed states are the same as 1.

3. A measurement of a plurality of physical properties of an object in which the energy source energizes the resonant structure over a tunable band of frequencies that includes the perturbed and unperturbed resonant frequencies of the resonant structure. The detection means determines the differences between the characteristics of the perturbed and unperturbed resonant oscillations of the resonant structure as the energy source is tuned through perturbed and unperturbed resonant frequencies.

The microwave embodiment of the invention has as its objects:

1. The simultaneous or sequential detection of more than one physical property of objects. 2. Simplifying microwave resonant frequency sensors by eliminating the need for swept frequency oscillators.

3. The accurate measurement of resonant frequency shifts in lower Q structures.

4. The simplified microwave signal processing obtained by using the dc voltage or current properties of a microwave source as the outputs of the sensor.

5. The realization of a highly accurate technique for simultaneous or sequential measurement of two different physical properties in a manner well described by an analytic theory.

DETAILED DESCRIPTION

A description is given below of example sensors that make use of the concepts of the invention. For clarity, this begins with a definition of the term object. This is followed by physical descriptions of each of the systems that utilize wave oscillations in all the forms of interest which include microwaves, electric fields, magnetic fields, laser light and acoustic waves. Finally, a very detailed description is given of illustrative microwave systems that are well modeled by an analytic theory and from which experimental data has been obtained to demonstrate the capabilities of the invention.

DEFINITION OF THE TERM OBJECT

It is possible by the methods described in this invention to measure multiple physical properties of an object. The object can be of simple form such as a homogeneous, cylindrical fiber in which case the measured properties could be size and the wave refractive properties of the material which, in the case of electromagnetic waves, would be in terms of the dielectric constant. The object can be more complex and be an inhomogeneous material in which case, average values of more than one parameter such as described above would be obtained. An example of an inhomogeneous case would be a bundle of ten fibers, each with different properties which, when measured, would yield some average value of the whole bundle. A rather complex example for a measured object could be the abdomen area of a pregnant woman in which acoustic waves could be used to measure multiple properties of the enclosed fetus such as its density or moisture content or other relevant properties. With a directed oscillations energy source scanned over such a complex object, the measured results could be presented in the form of an actual picture, perhaps displayed on the screen of a cathode ray tube. Another example of a complex object could be a harbor scene for an approaching boat in the fog. For a scanned resonant circuit sensor, this scene could also be presented as a cathode ray tube picture.

PHYSICAL DESCRIPTIONS

All of the systems are comprised of the following elements. A resonant structure is excited into oscillation by an energy source. An object is placed so that it interacts with the polarized oscillations of the resonant structure and perturbs these oscillations. Detection is achieved by measuring the perturbed and unperturbed properties of the oscillations themselves or of quantities affected by these oscillations.

Microwave Systems

Figure 1A:
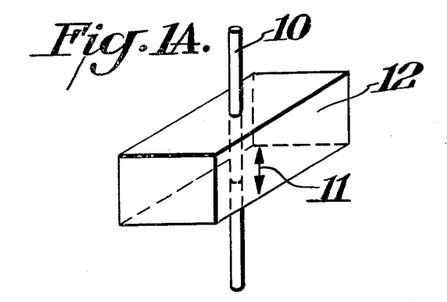
FIG. 1A is a diagrammatical representation showing an example object in the form of a dielectric rod inserted into a $TE_{101}$ mode rectangular microwave cavity parallel to the electric field polarization.
Figure 1B:
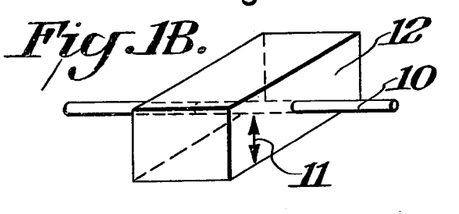
FIG. 1B is the same as FIG. 1A except that the dielectric rod is inserted perpendicular to the electric field polarization.
Figure 2:
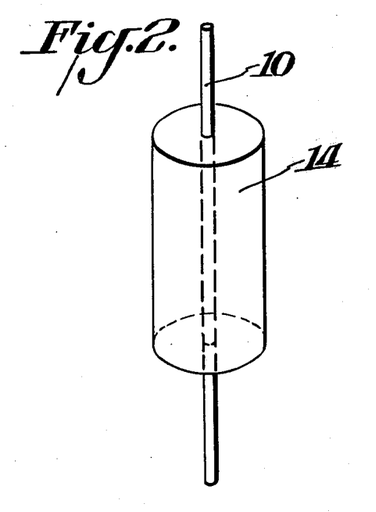
FIG. 2 is also a diagrammatical representation as in FIG. 1A and B except that the microwave cavity has a cylindrical shape and the dielectric rod object is inserted along the central axis of the cavity.

Beginning with FIG. 1A, 10 is an example object of cylindrical shape whose physical properties are to be measured using microwaves, Its cylindrical axis is parallel to the polarization direction 11 of the electric field component of the electromagnetic, resonant oscillations in the $TE_{101}$ mode, rectangular resonant cavity 12. FIG. 1B shows the example object 10 with its axis at right angles to the electric field polarization 11. FIG. 2 shows a cylindrical resonant cavity 14 with the example object 10 aligned with the cavity's cylindrical axis.

Referring now to FIGS. 11, 3, 4, 5, 6 and 7, a Gunn flange 16 and a conducting end plate 17, form the end walls of a rectangular cavity held together by screws 18. The iris slot 20 cut into the Gunn flange 16 allows energy to be communicated between the Gunn device energy source 22 and the resonant cavity and the detection means. The circular hole 24 in the Gunn flange 16 serves as part of a filter that prevents electromagnetic energy generated at the Gunn device 22 from leaking out of the Gunn flange 16 through the aluminum rod dc bias post 26 to the electric dc power supply 27. The well 28 in the top of the Gunn flange holds adhesive fastening the bias post 26 to the Gunn flange 16. 29 is an electric resistor connected between the dc power supply 27 and the dc bias post to provide a detection means. The actual detection with this resistor 29 is accomplished with the electrical voltmeter or ammeter 33 that measures either the dc voltage across the resistor 29 or the dc current through it.

Figures 4, 7:
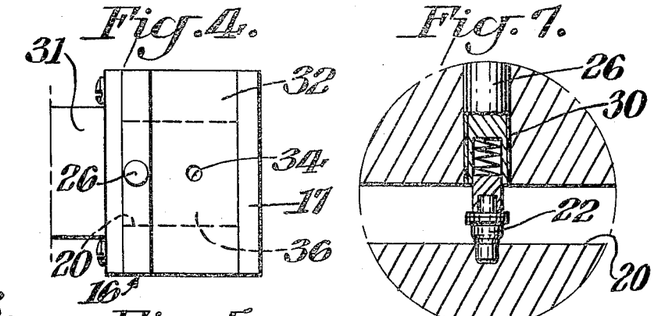
FIG. 4 is a top view of the microwave cavity oscillator shown in FIG. 3 showing the relative position of the cavity, the Gunn flange and the waveguide.
FIG. 7 is an enlarged view of the center section of the front view of FIG. 3 showing the details of the Gunn device mounting.

FIG. 7 shows details of how the Gunn device 22 is attached to the Gunn flange 16. A spring-loaded, metal sleeve 30 at the bottom of the dc bias post 26 relieves stress on the Gunn device 22 arising from thermal expansion of the Gunn flange elements as the apparatus heats up during use. The dc bias post 26 is electrically insulated from the Gunn flange 16 by a layer of tape wrapped around the post. 32 is the metallic, conducting sidewalls of the rectangular cavity through which a cylindrical hole 34 has been drilled to allow the object 10 to be inserted so that it interacts with the resonant oscillations. 36 is the rectangular slot cut through these sidewalls 32 to form part of the cavity.

Rectangular waveguide 31 communicates electromagnetic energy to a detection means that can be used instead of or in addition to the detection with the resistor 29 and the electrical meter 33. The microwave attenuator 35 reduces the power so that no damage is produced in this alternate detection means 37 which is a microwave frequency counter, power meter, or phase meter.

Referring to FIGS. 8, 9, and 10, 40 is a cylindrical cavity to which the Gunn flange 16 and rectangular waveguide 31 have been fastened with screws 18. 42 is the collar of this cavity 40, in which threaded holes have been fashioned to accept the screw fasteners 18. 44 are circular holes made in the cavity walls to allow insertion of the object 10 so that it can interact with the resonant oscillations. 46 is a rectangular slot cut through the collar 42 and the cylindrical cavity 40 that allows electromagnetic energy to be communicated between the Gunn flange 16 and the cylindrical cavity 40. 26 is again the insulated dc bias post.

Figure 3:
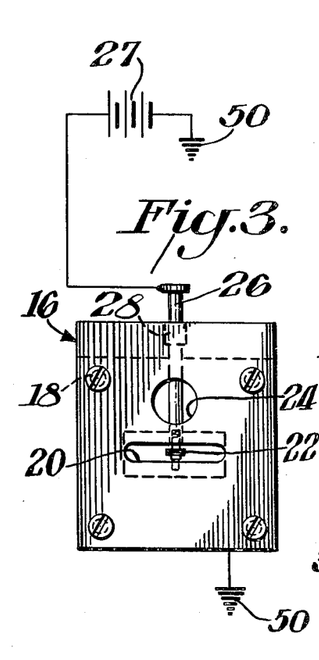
FIG. 3 is a front view of a microwave cavity oscillator showing the front face of the Gunn flange.
Figure 11:
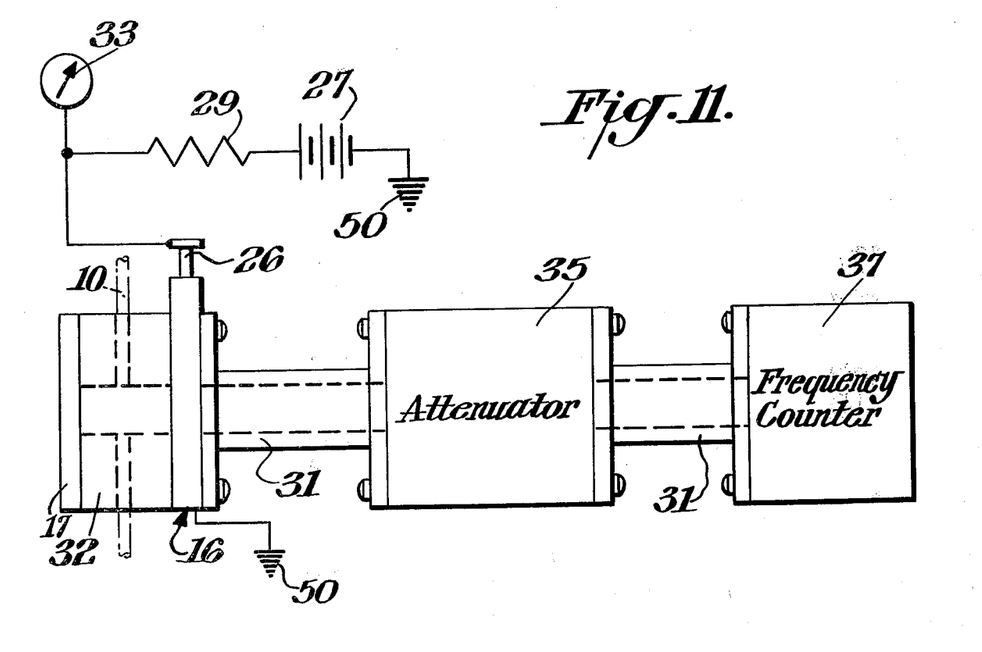
FIG. 11 is a layout of a complete microwave sensor circuit showing the connections between the detection means and the oscillator and the energy source.

FIG. 11 shows a layout of a complete microwave detection system. The rectangular cavity, consisting of the cavity side walls 32 and end plate 17, are connected to the Gunn flange 16. The Gunn flange is connected to an electrical ground 50 and its bias post 26 is attached to a dc power supply 27 and ground 50 through the electrical resistor 29 and the meter 33. The items 29 and 33 serve as the detection means. Interaction between the object measured 10 and the resonant circuit oscillations is obtained by inserting the object 10 through the cavity side walls 32 into the cavity. Alternate detection is achieved by communicating the electromagnetic energy from the Gunn flange 16 through rectangular waveguide 31 and the attenuator 35 to the detection means 37 which is a frequency counter, power meter, or phase meter. If this alternate detection is alone desired, then the resistor 29 and meter 33 can be eliminated between the bias post 26 and the dc power supply 27 as shown in FIG. 3. If use of the cylindrical cavity is desired, then the rectangular cavity side walls 32 and end plate 17 are replaced by the cylindrical cavity 40 and its connection collar 42 being attached to the Gunn flange 16.

Electric and Magnetic Field System

Referring next to FIGS. 20, 21A, 21B, 22A and 22B, a representative system is given for a sensor where the interaction between the object 72 and 78 and the resonant oscillations, is for oscillations in the form of electric and magnetic fields. 48 is an operational amplifier with negative 60 and positive 58 inputs and an output 56. This amplifier 48 is the source of energy for the resonant oscillations. The ground connections 50 and the feedback of the output 56 through the potentiometer 54 and the nonlinear resistance 52 provides the correct conditions for oscillations to occur with the resonant circuit. The resonant circuit is comprised of a capacitor 68, and inductor 64 and a resistor 66. Detection is accomplished by attaching a frequency counter, an ac voltmeter, or a phasemeter to the output terminal 62.

Figure 21A:
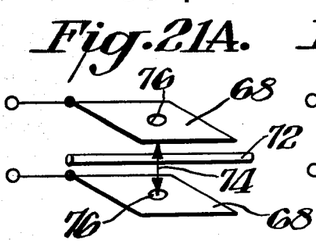
FIG. 21A is a representation showing the interaction between the polarized electric field of a capacitor and a rod shaped object perpendicular to the electric field.
Figure 21B:
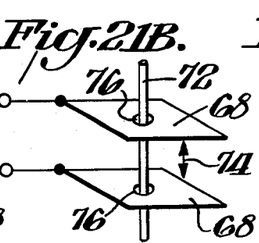
FIG. 21B is the same as FIG. 21A except that rod is shown parallel to the electrical field.

FIG. 21A shows an example object 72 of cylindrical shape inserted to interact with the electric field of the capacitor for a right angle orientation between the electric field polarization 74 and the object's cylindrical axis. FIG. 21B is the same except that the object 72 is inserted through circular holes 76 in the capacitor plates to have its cylindrical axis parallel to the electric field polarization 74.

Figures 22A, 22B:
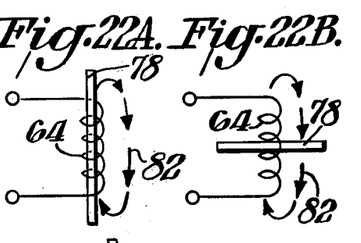
FIG. 22A is a representation showing the interaction of the polarized magnetic field of an inductor with the rod shaped object parallel to the magnetic field.
FIG. 22B is the same as FIG. 22A except the object is perpendicular to the magnetic field.

FIG. 22A shows an example object 78 of cylindrical shape inserted into the inductor 64 so that its cylindrical axis is parallel to the magnetic field polarization 82 of the inductor. FIG. 22B is the same as 22A, except the sample 78 has its cylindrical axis oriented perpendicular to the magnetic field polarization 82.

Laser System

Figure 23:
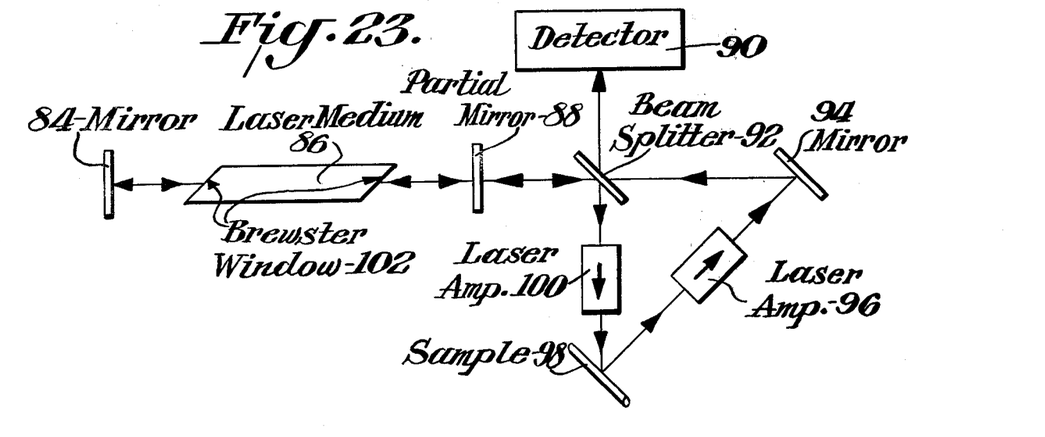
FIG. 23 is a representation showing a resonant circuit sensor where the resonant oscillations are in the form of electromagnetic fields of optical frequencies and the energy source is a laser medium.

Now reference is made to FIG. 23, which gives a representation of a detection system in which the oscillations are in the form of electromagnetic fields at optical frequencies. 86 is the laser-medium energy source that excites resonant oscillations in the sensor. The totally reflecting mirror 84 and the partially reflecting mirror 88 form the resonant cavity. The light that propagates through the mirror 88 allows the communication of light energy outside the cavity. 98 is an example object whose properties are measured. It could be inserted between the mirrors 84 and 88 to interact with the resonant oscillations such as shown for the microwave system of FIG. 11. However, as shown here, the object 98 is external to the resonant cavity. The light from the resonant cavity reflects off the beam splitter 92 down through a laser amplifier 100 before it strikes the object 98. After the light has interacted with the object, it passes again through a laser amplifier 96 and is directed by a mirror 94 back through the beam splitter 92 and into the resonant cavity where this reflected beam interacts with the resonant circuit oscillations. A part of the light energy is reflected from the beam splitter up to the detection means 90 which is a frequency (or wavelength) detector, a power detector, or a phase detector. Polarization of the light oscillations relative to the object 98 is produced by the polarizing Brewster windows 102 contained in the resonant cavity. Different polarization orientations are obtained by rotating the alignment of the Brewster windows 102 relative to the object 98. An important generalization shown in this system is that the object can be external to the resonant cavity. The amplifiers 96 and 100 only serve to increase the amplitude of the oscillations before and after it has interacted with the object. If the signal strength of the oscillation is strong enough, one or both of these amplifiers may not be needed.

Acoustic System

Figure 24:
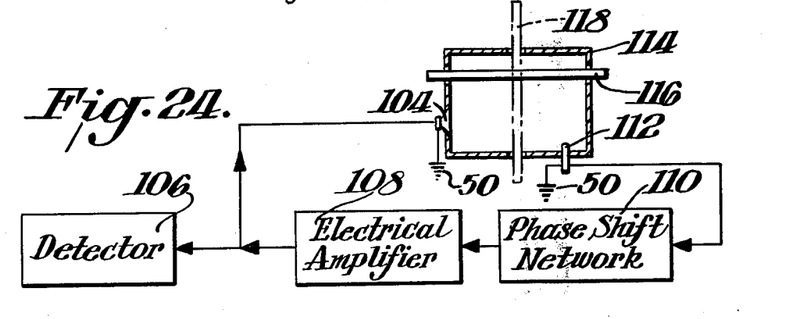
FIG. 24 is a diagram of a resonant circuit sensor where the sample interacts with the resonant circuit oscillations in the form of acoustic waves.

FIG. 24 gives a representation of a sensor system in which the resonant oscillations are in the form of acoustic waves. 108 is the electrical amplifier that is the energy source for the oscillations. The speaker 104 converts the ac electrical signal into acoustic waves that excites oscillation in the acoustic resonant cavity 114 of rectangular shape. The microphone 112 converts the acoustic waves back into ac electrical signals. The phase shift network 110 provides the correct phase for the ac electrical signal to allow resonant oscillations to occur in the resonant cavity. An example object is shown oriented with its long axis parallel 116 and perpendicular 118 to the long dimension of the cavity to provide two relative orientations between the acoustic wave polarization and the object. Detection is accomplished by connecting a frequency counter, voltmeter or phase meter 106 to the electrical output of the amplifier 108. Electrical grounds 50 provide appropriate conditions for the sensor's operation.

DETAILS OF MICROWAVE DETECTOR SYSTEMS

Figure 5:
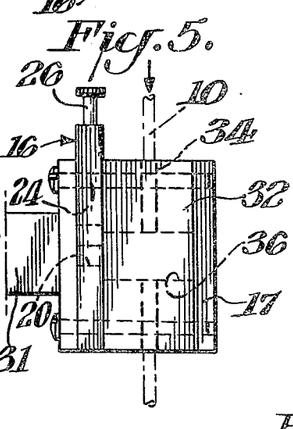
FIG. 5 is a side view of the device shown in FIG. 3, with the example object inserted into the cavity.
Figure 6:
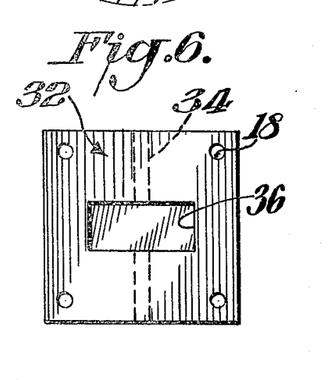
FIG. 6 is a front view of the microwave oscillator cavity with the Gunn flange and waveguide removed.

FIGS. 1 and 2 show example microwave resonant cavities of rectangular 12 or cylindrical 14 shape that can be used to construct the sensor. These cavities operate in either the transverse electric (TE) or transverse magnetic (TM) modes. Integer subscripts such as 101 or 112 when listed with the abbreviations TE or TM specify a particular order mode. The cavity walls are constructed of a good electrical conductor. Communication with the cavity is established through holes cut in the cavity walls. Interaction between the microwave fields and sample objects 10 is either interior or exterior to the cavity. Object shapes are arbitrary and object state can be solid, liquid or gas phase. The medium through which the oscillations propagate as discussed here is a gas, but it can as well be a vacuum, a liquid or a solid. Interaction of interior microwave fields with an object 10 such as a dielectric rod is obtained by inserting the object through the holes 34 such as shown in FIG. 5. With such interior interaction, loss of needed microwave energy outside the cavity can be minimized by placing object communication holes 34 at locations where minimum disturbance of cavity surface current is obtained. The loss of microwave energy outside a cavity reduces the quality or Q of the cavity and affects the cavity's performance. Exterior interaction or a combination of exterior and interior interaction between objects and microwave fields can be obtained by placing communication hole or holes at points where increased radiation is obtained. The object can then be completely external to the cavity and coupling structures such as antennaes or horns can be used to channel microwave energy between the microwave circuit and the material. An example of external interaction with electromagnetic oscillations at optical frequencies is shown in FIG. 23.

Figure 8:
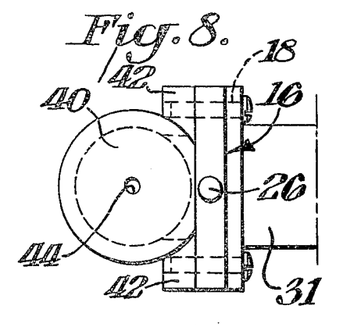
FIG. 8 is a top view of a cylindrical cavity microwave oscillator showing the relative position of the waveguide, Gunn flange and cavity.
Figure 9:
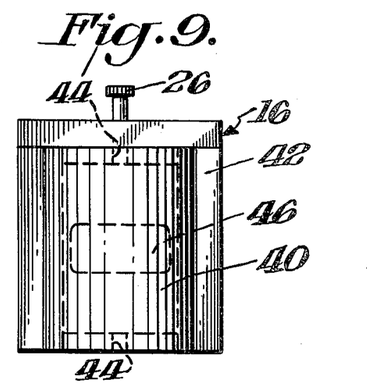
FIG. 9 is a front view of the cylindrical cavity microwave oscillator shown in FIG. 8.
Figure 10:
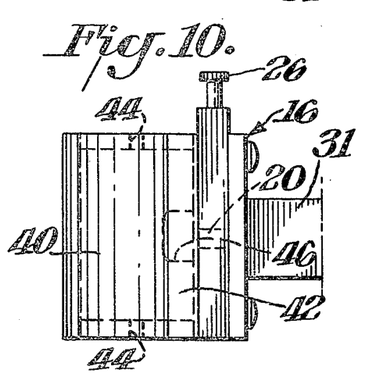
FIG. 10 is a side view of the cylindrical cavity microwave oscillator shown in FIG. 8.

For a passive resonant circuit, excitation is by an external microwave source through a communication hole (or iris such as 20 with the Gunn device 22 and bias rod 26 removed) through which an object may or may not also be inserted. Active resonant circuits are obtained by incorporating a microwave source structure into the cavity itself. An illustrative Gunn (or IMPATT) device flange 16 used for incorporating a source 22 is shown in FIG. 3. This flange 16 consists of a metal plate in which holes 20 and 24 have been cut to incorporate a microwave emitting device 22 (such as a Gunn or IMPATT device) and to fasten it to a microwave resonant circuit, such as the rectangular cavity formed by 32 and 17. The expanded view (See FIG. 7) of the center section shown in FIG. 3 shows the device 22 mounted at the bottom of a slot 20 with electrical contact to its top provided by a spring loaded, aluminum rod 26 insulated with tape. This insulated rod 26 along with the large hole 24 above the device 22 (shown in the front view of FIG. 3), serve as a low pass filter to restrict the transmission of microwave energy to external circuits. An oscillating resonant circuit is obtained by incorporating such a flange into rectangular (32 and 17) or cylindrical (40 and 42) cavities as shown in FIGS. 4 and 8.

DETECTION MEANS

Sensing of an object's properties is obtained by detecting properties of the resonant circuit as described below. For passive circuits, an external oscillator is used to excite the cavity over a band of frequencies. The detected circuit properties include the resonant frequency and changes in its value, and the amplitude of microwave fields excited inside the cavity or reflected back from the cavity at any of the swept frequencies, and any changes in these amplitudes. For active circuits, the detected properties include the frequency of oscillation, signal amplitude, the dc current or voltage (such as measured with 33) at the terminals of a device structure like the Gunn flange 16 of FIG. 3, and any changes in any of these quantities. A diagram of a complete detecting system is shown in FIG. 11. Connection between the cavity (32 and 17), the attenuator 35 and the microwave counter 37 can be by any microwave propagating method such as a waveguide 31 between the Gunn flange 16 and the attenuator 35 and between the attenuator and the counter 37. Another possibility would be connection through co-axial cable or through a combination of co-axial cable and waveguide interfaced with suitable transitions. Since the active circuit oscillates at the resonant frequency of the cavity and since the counter detects any small changes in this oscillation, resonant circuit structures of rather low Q can be used. If such low Q structures were used in passive configurations, the amplitude response near resonance would be so broad and shallow that accurate determination of $\Delta f$ could not be obtained. A significant advantage in measuring $\Delta f$ at lower Q's is thus obtained with the active circuits. Detection of signal amplitude of active circuits can be obtained by connecting a microwave power meter in place of (or in addition to) the counter 37 indicated in FIG. 11.

Figure 12:
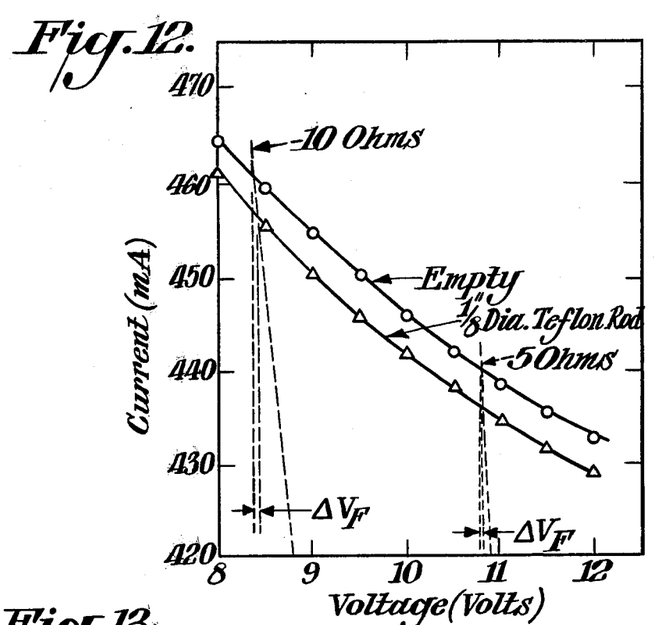
FIG. 12 is a graph showing a shift in the current and voltage characteristics above threshold for a Gunn flange attached to a 0.75 inch long rectangular cavity as shown in FIG. 11 when a Telfon ® rod is inserted into the cavity. The specified 0.75 inch length is the distance between the Gunn flange and the conducting end plate.

Detection of dc current or voltage of device structures like Gunn flanges is illustrated by the experimental data of FIG. 12. Here the dc current-voltage characteristics of the dc bias terminal relative to the grounded flange 50 structure are shown for the rectangular cavity of FIG. 4 (with a Gunn device 22 inside the flange 16). As shown, insertion of one-eighth inch diameter Teflon ®rod as an object 10 causes the current to change at the indicated operating voltages of the flange. Convenient detection is obtained by connecting the flange in series with a resistor 29 and a constant voltage dc power supply 27. The load lines and the flange voltage change $\Delta V_f$ obtained with a 13 volt supply 27, with 5 and 10 ohm series resistors 29, and a voltmeter 33 are shown.

PARAMETER SEPARATION

A primary mode for sensing more than one parameter is obtained by detecting resonant frequency shifts of either active or passive resonant circuits for different orientations of microwave fields and the sensed object. This scheme, implemented for simultaneous or sequential measuring of two physical properties is described theoretically and illustrated with experimental data. An additional technique for two property sensing with a combination of $\Delta f$ and $\Delta I$ monitoring is also described.

$\Delta f$ Parameter Separation Theory

This theory models resonant frequency shifts of a cavity disturbed by the insertion of an object when the microwave electric field is either parallel or perpendicular to some feature of the object. As an example, a non-magnetic object 10 with a rod shape is analyzed here even though objects with arbitrary shapes and magnetic properties can be used. If the volume of the object $V_s$ is small compared to the volume of the air-filled cavity $V_c$, then standard perturbation theory gives such a frequency shift $\Delta f$ for non-magnetic samples as $$\frac{\Delta f}{f_o} = \frac{\epsilon_o(\epsilon' - 1) \int_{V_s} \vec{E}_o \cdot \vec{E}_p dV}{\int_{V_c} (\epsilon_o \vec{E}_o \cdot \vec{E}_o - \mu_o \vec{H}_o \cdot \vec{H}_o) dV} \quad (1)$$

where $\epsilon_o$ and $\mu_o$ are the permittivity and permeability of free space respectively, $f_o$ is the resonant frequency of the unperturbed cavity, and $\epsilon'$ is the relative (and real) permittivity of the sample. The E's and H's are respectively the electric and magnetic fields with the subscripts "o" and "p" denoting unperturbed and perturbed values. The subscript $V_s$ and $V_c$ by the integral signs indicate integration over these respective volumes. When $f_o$ exceeds the perturbed frequency, $\Delta f$ is taken as positive.

For a rectangular cavity 12 resonating in the $TE_{101}$ mode, a cylindrical object 10 can be inserted into the center of the cavity through small holes 34 so that it is parallel to the maximum electric field [1,4,5] as shown in FIG. 1A. Substitution into Eq. 1 then gives $$\Delta f/f_o = 2(\epsilon' - 1)(A_s b/V_c) \quad (2)$$

where $V_s = A_s b$ and $A_s$ and b are respectively the cross-sectional area of the sample and the height of the cavity. For the object 10 inserted perpendicular to the maximum electric field as shown in FIG. 1B, the frequency shift is $$\frac{\Delta f}{f_o} = \frac{2(\epsilon' - 1)}{(\epsilon' + 1)} \frac{A_s a}{V_c} \quad (3)$$

where a is the width of the cavity since $V_s = A_s a$. This gives two independent equations in $\epsilon'$ and $A_s$ for the frequency shift.

Similar results can be obtained with a cylindrical cavity 14 for the object 10 inserted along the cavity axis as shown in FIG. 2. For this cylindrical case, the frequency shift relations are expressed in terms of Bessel functions. A given Bessel function is identified as one of several different kinds of solutions to the general class of Bessel differential equations of a particular order as referred to below. If the cavity is excited in the $TM_{010}$ mode, the electric field is parallel to the object 10 [3,4]

and the frequency shift, specified by Eq. 1, simplifies to $$\frac{\Delta f}{f_o} = \frac{(\epsilon' - 1)}{2J_1^2(\chi)} \frac{A_s l'}{V_c} \quad (4)$$

where $l'$ is the length of the cavity and $J_1(\chi)$ is the first order Bessel function of the first kind. To satisfy the boundary conditions for this mode [3,4], $\chi$ must be the first zero of the zeroth order Bessel function of the first kind. This gives a value of $\chi = 2.405$. This completely specifies $J_1(\chi)$ to have the value 0.5191. These Bessel function values are obtained from standard tables.

If this cavity is excited in the TE$_{112}$ mode, the electric field becomes perpendicular to the sample and the frequency shift is given by $$\frac{\Delta f}{f_o} = \frac{\epsilon' - 1}{\epsilon' + 1} \frac{1}{2(1 - 1/\chi^{*2})J_1^2(\chi^*)} \frac{A_s l'}{V_c} \quad (5)$$

where $\chi^*$ is the first zero of the derivative of the first order Bessel function of the first kind and has the value $\chi^* = 1.841$. This gives $J_1(\chi^*)$ the value 0.5819 [6]. Once again two independent equations in $\epsilon'$ and $A_s$ are obtained.

Identification of which of the various cylindrical modes is being excited can be accomplished by monitoring the resonant frequency. The unperturbed resonant frequency $f_o$ for any TE$_{mnp}$ or TM$_{mnp}$ mode in a cylindrical cavity is given by [4,7]

$$f_o(m,n,p) = \frac{1}{2\sqrt{\mu_o \epsilon_o}} \sqrt{\frac{\chi_{mn}^2}{\pi^2 r^2} + \frac{p^2}{l^2}} \quad (6)$$

where $r$ is the radius of the cylindrical cavity. For TM modes, $\chi_{mn}$ is the n-th zero of the m-th order Bessel function of the first kind. For TE modes, $\chi_{mn}$ is the n-th zero of the derivative of the m-th order Bessel function of the first kind. Accordingly, $\chi_{01}$ for the TM$_{010}$ mode has the $\chi$ value given above (i.e. $\chi_{01} = \chi = 2.405$). For the TE$_{112}$ mode, $\chi_{11}$ has the $\chi^*$ value also given above (i.e. $\chi_{11} = \chi^* = 1.841$).

To separate the variables $\epsilon'$ and $A_s$ from measured $\Delta f$ values, two independent equations must be solved. For the rectangular cavity case, solution of Eqs. 2 and 3 gives $$\epsilon' = \frac{a}{b} \frac{[V_c(\Delta f/f_o)]_\parallel^r}{[V_c(\Delta f/f_o)]_\perp^r} - 1 \quad (7)$$

where the superscripts r refer to the rectangular cavity and the subscripts $\parallel$ and $\perp$ respectively identify which measured $\Delta f/f_o$ values were obtained for the electric field parallel and perpendicular to the sample. If the same size cavities or a single cavity is used for both the parallel and perpendicular measurements, the cavity volumes $V_c$ of course cancel out. Substitution of $\epsilon'$ back into either Eq. 2 or 3 then gives the object cross-sectional area $A_s$.

Similarly for the cylindrical cavity cases $$\epsilon' = \frac{[J_1^2(\chi)V_c(\Delta f/f_o)]_{TM}^c}{[J_1^2(\chi^*)V_c(1 - 1/\chi^{*2})(\Delta f/f_o)]_{TE}^c} - 1 \quad (8)$$

where the subscripts specify the values applicable for the TM$_{010}$ and TE$_{112}$ modes and where the superscripts c identify the cylindrical cavity. Again, if the same cavity is used for both modes, the cavity volumes $V_c$ cancel. Substitution of this $\epsilon'$ value back into either Eq. 4 or 5 gives the object size $A_s$. Other combinations of independent equations (such as Eqs. 2 and 5 or Eqs. 3 and 4 or different expressions for other modes) that have the electric field parallel or perpendicular to the object can also be used to separate these variables.

Example $\Delta f$ Parameter Separation Systems

A rectangular cavity 12 designed to operate at a frequency of around 9 Gigahertz (GHz) in the TE$_{101}$ mode [4] has a width of 0.9 inch, a height of 0.4 inch, and a length of 0.9 inch. At the center of opposing broad and narrow walls, one-eighth inch holes 34 are drilled to allow object 10 insertion like that shown in FIG. 1(A) and 1(B). A Gunn flange 16 [8-10] is used to replace one of the end walls. The configuration of the resulting system is essentially the same as that shown in FIG. 11 except for the longer cavity length (the distance between 16 and 17 in FIG. 11). The details of the X-band flange are given in FIGS. 3 and 7. A Microwave Associates Gunn device MA49158 with a 9 GHz center frequency can be used as the energy source 22 in the flange 16. The flange 16 is oriented so that its bias terminal 26 (see FIG. 3) is parallel to the vertical direction (see FIG. 1) and so that its iris 20 (see FIG. 3) is centered at the cavity end. This oscillator is attached to a frequency counter 37 (for example a EIP Model 350D) through an attenuator 35 and to a dc power supply 27 (for example 0-12 V, 1.0 A) as shown in FIG. 11. For this case the resistor 29 and the meter 33 are eliminated as indicated in FIG. 3. With such a cavity controlled oscillator, the resonant frequency shifts are read directly from the counter 37.

When a cavity controlled Gunn oscillator is excited, the physical length of the cavity is observed to be slightly different from the half guided wavelength of the oscillating frequency due to the reactance of the Gunn device 22. This difference tends to slightly alter the observed frequency shifts (see Equation 2 and 3) so that the observed data $(\Delta f/f_o)_{OBS}$ is related to the theoretical value $(\Delta f/f_o)_{TH}$ by $$(\Delta f/f_o)_{TH} = K(\Delta f/f_o)_{OBS} \quad (9)$$

where K is a correction factor approximately equal to one.

A single cylindrical cavity 14 [4] is designed to oscillate at 8.8 GHz in the TM$_{010}$ mode and at 10.3 GHz in the TE$_{112}$ mode by selecting a radius of 0.5 inch and length of 1.5 inches. One eighth inch holes 44 as shown in FIG. 8 are made at the center of the cavity ends to allow object insertion. Little radiation loss occurs through these or the rectangular cavity holes since interruption of current flow lines is minimal. Incorporation of the Gunn flange 16 onto the cylindrical cavity involves cutting a rectangular iris 0.405 inch by 0.980 inch 46 half way along the length l of the cavity so that the longer iris dimension is perpendicular to the cavity axis. This is connected to the power supply and frequency counter as indicated in FIG. 11.

The mode of cavity oscillation is identified by noting whether 8.8 or 10.3 GHz oscillations are obtained. Switching between the modes is obtained by inserting lossy material (graphite pencil lead) part way into the cavity and withdrawing it at various angles. If the lead is removed parallel to the cavity axis, the vertical component of the $TM_{010}$ electric field is heavily attenuated and TE oscillation is obtained. Withdrawing the lead at large angles to the cavity axis, attenuates the radial component of the $TE_{112}$ mode so that TM oscillations are produced. This switching capability makes the cylindrical configuration more versatile but less stable than the single mode rectangular cavity system. As with the rectangular cavity controlled oscillator, a correction factor K line in Eq. 9 is also required for cylindrical cavity controlled systems. Since the field patterns of the $TM_{010}$ and $TE_{112}$ modes are quite different [4,5] each mode could be expected to have a different K factor.

Δf Experimental Results

Figure 13:
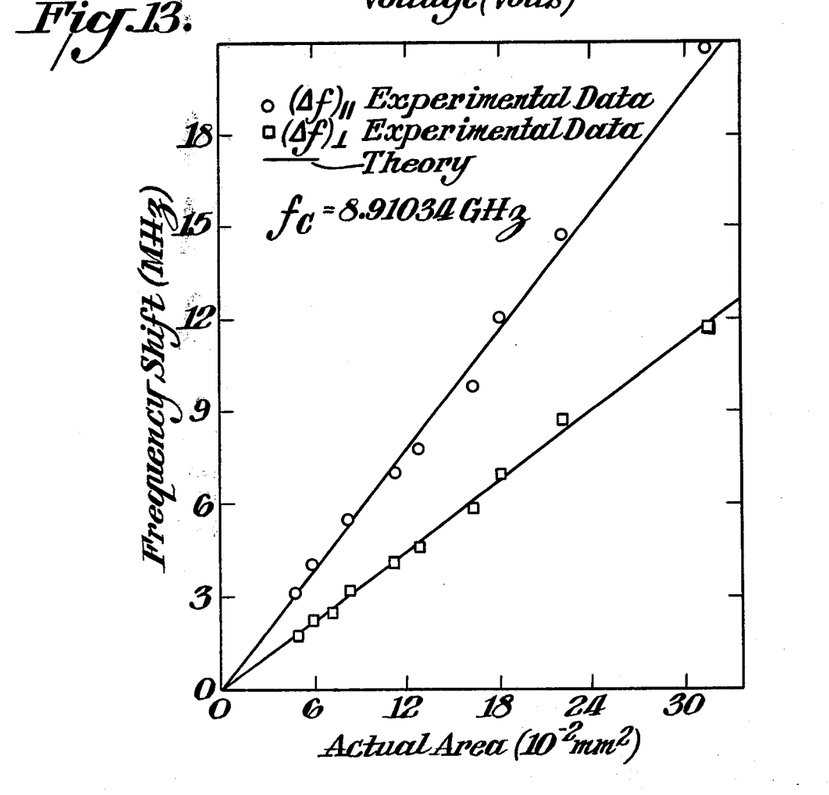
FIG. 13 is a graph of the theoretical and experimentally observed frequency shifts as a function of actual area for nylon monofilaments in a $TE_{101}$ mode rectangular cavity.

A comparison between the theoretically predicted and experimentally observed frequency shifts with the rectangular oscillator is shown in FIG. 13 as a function of the actual cross-sectional area of the objects obtained by measuring the diameters with a precision micrometer. These data are for rod shaped nylon objects inserted parallel and perpendicular to the microwave electric field. The observed frequency shift data are in excellent agreement with the solid lines representing the theoretical values specified by Equations 2 and 3 as modified by the K factor of Eq. 9. The value of the rectangular system K factor, and the K factor values for the cylindrical Gunn flange oscillators are given in Table I. As noted previously, these factors are close to one.

TABLE I

Value of the frequency shift correction factor K for the rectangular and cylindrical cavity Gunn flange oscillators

| Cavity Type | Mode | K |
| --- | --- | --- |
| Rectangular | $TE_{101}$ | 0.980 |
| Cylindrical | $TM_{010}$ | 0.990 |
| Cylindrical | $TE_{112}$ | 0.993 |

Figure 14:
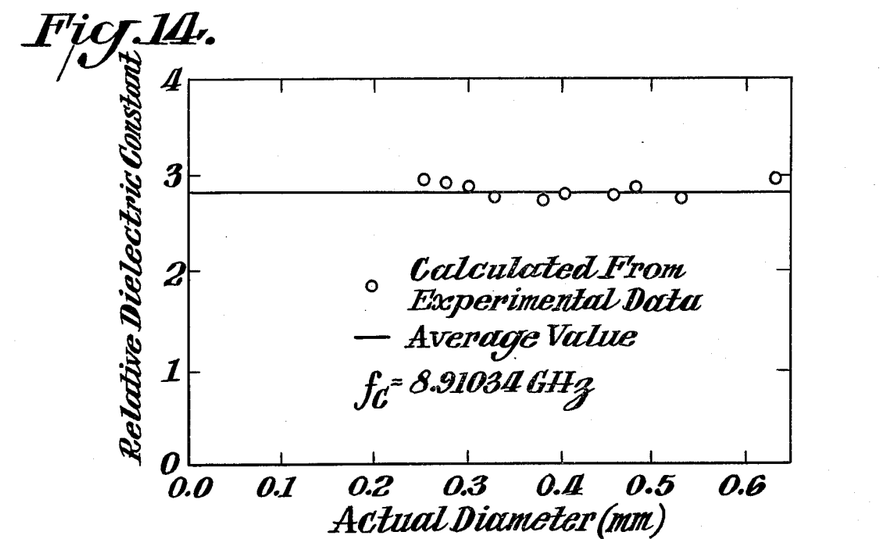
FIG. 14 is a graph of the calculated relative dielectric constant vs. actual diameter for nylon monofilaments in $TE_{101}$ mode rectangular cavity.
Figure 15:
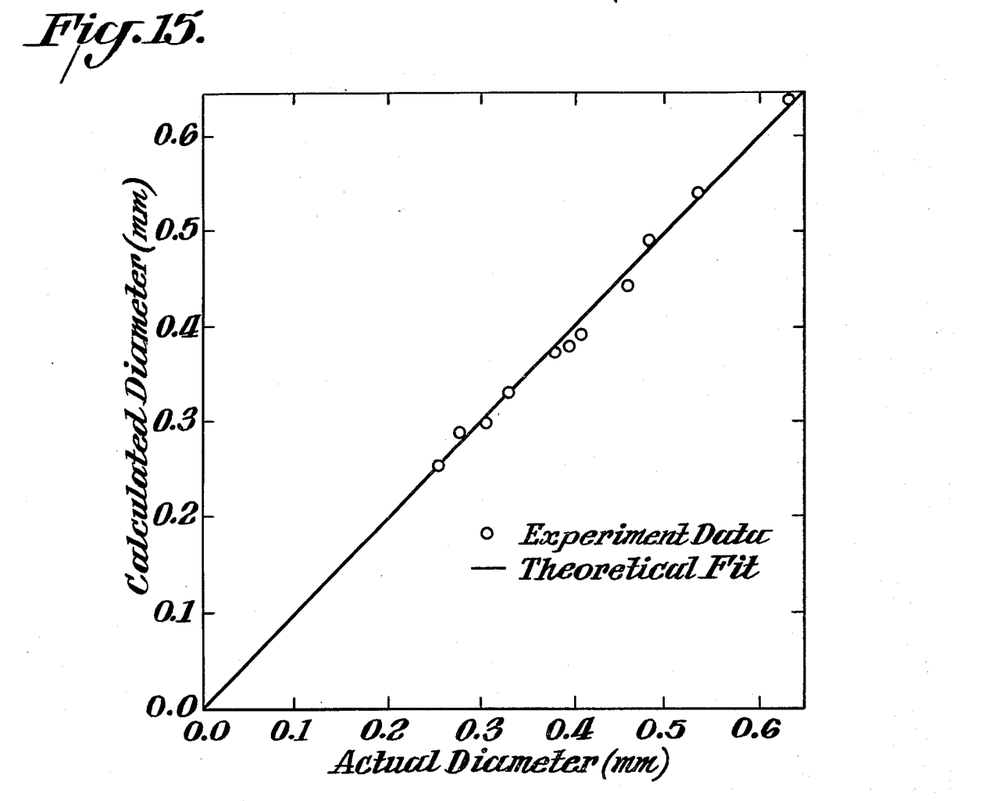
FIG. 15 is a graph of the calculated diameter vs. actual diameter for nylon monofilaments in $TE_{101}$ mode rectangular cavity.

The ability of these systems to separate sample size and dielectric constant is demonstrated in FIGS. 14 and 15. In FIG. 14, the measured dielectric constant for nylon material (calculated from Eq. 7) is presented as a function of the actual object diameter measured with a precision micrometer. This requires that each object 10 be inserted through the one-eighth inch holes both parallel and perpendicular to the electric field as indicated in FIGS. 1A and 1B. Inspection of Eq. 7 shows that the correction factors K cancel out of this expression for the rectangular system since the same mode is used for both frequency shift measurements.

The solid line in FIG. 14 is the average value of the measured data. The root-mean-squared difference between the data points and this mean value of 2.86 is 0.076 or 2.6 percent of the mean. This 2.86 relative dielectric constant value lies within the nominal range of 2.5 to 3.5 given for nylon [11]. The close fit between the cavity - measured diameters and the actual diameters is shown in FIG. 15. The root-mean-squared percent error in the microwave measured data was 2.0 percent. A summary of the accuracy for the ε' and sample size values obtained from nylon, Teflon ®, and quartz samples using both the rectangular and cylindrical cavity systems is given in Table II. Published values for the relative dielectric constants used as the correct values are 3.8 for quartz [5] and 2.08 for Teflon ®[5,11]. Inclusion of the K correction factors into Eq. 8 gives $$\epsilon' = \frac{[J_1^2(\chi)V_c(\Delta f/f_o)K]_{TM}^c}{[J_1^2(\chi^*)V_c(1 - 1/\chi^{*2})(\Delta f/f_o)K]_{TE}^c} - 1.$$

TABLE II

The percent error or the percent difference from the mean obtained for the simultaneous measurement of sample size and dielectric constant using both the rectangular and cylindrical cavity Gunn flange oscillators.

| | | Percent Error | | | |
| --- | --- | --- | --- | --- | --- |
| | | Rectangular Cavity ($TE_{101}$ Mode) | | Cylindrical Cavity ($TM_{010}$ & $TE_{112}$ Modes) | |
| Material | No. Samples Measured | Size | ε' | Size | ε' |
| Nylon | 10 | 2.0[a] | 2.6[b] | 2.9[a] | 3.1[b] |
| Quartz | 3 | 2.3[a] | 4.2[a] | 1.2[a] | 3.0[a] |
| Teflon | 1 | 2.8 | 4.5 | 2.7 | 0.7 |

[a]Root-mean-squared percent error.
[b]Root-mean squared percent difference from the mean.

Since $K_{TM}/K_{TE} = 0.997$, this K factor adjustment makes little difference in the ε' values obtained.

Figure 16:
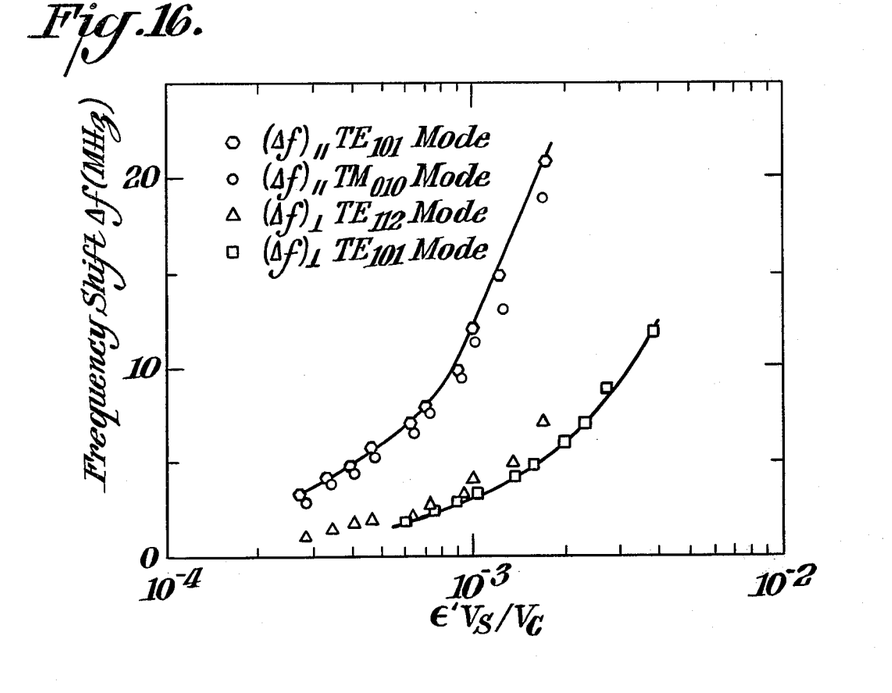
FIG. 16 is a graph of the frequency shift vs. the product of the dielectric constant times sample volume normalized to the cavity volume for nylon monofilaments in rectangular and cylindrical cavities.

Good frequency shift detection sensitivity (Δf>1 MHz) is obtained when the ratio of the sample to cavity volume times the relative dielectric constant (ε' $V_s/V_c$) is greater than $2(10^{-4})$ as shown in FIG. 16. This shows that the relative frequency shifts (Δf/$f_o$) are of the same order of magnitude for all the systems studied as described by the theoretical expression described above. To satisfy the small disturbance assumption, these values should probably remain below 1% (i.e., $10^{-2}$). Proper choice of cavity frequency (and thus its size) should assure operation in this range for arbitrary sample size. Accurate parameters measurements were obtained for strands as well as rod-shaped samples indicating that other than the theoretically ideal cylindrical shape can be measured.

As seen from Table II, measurement accuracies on the order of 2 to 5 percent are obtained using the Gunn flange oscillator systems. The worst single case error is 5.6 percent. When an IMPATT diode is substituted for the Gunn device in the X band flange and properly biased, similar results are obtained. Passive cavity measurements of the frequency shifts also give comparable but lower accuracy results (±10%). For the passive measurements, the Gunn flange 16 is replaced with a small iris; and the cavity is connected to a microwave sweeper. The resonant frequency shift is obtained by observing the frequency (or frequencies for the cylindrical cavity) where minimum microwave energy is reflected from the cavity. Resonant frequency determination in this manner is less accurate than just reading the frequency of a microwave counter as required with the active cavity systems. However, the passive, swept - frequency technique does have the advantage of enabling both the TM and TE mode resonant frequencies to be measured from a single sweep instead of the switching (or two cavities) required with the cylindrical Gunn oscillator.

Figure 17:
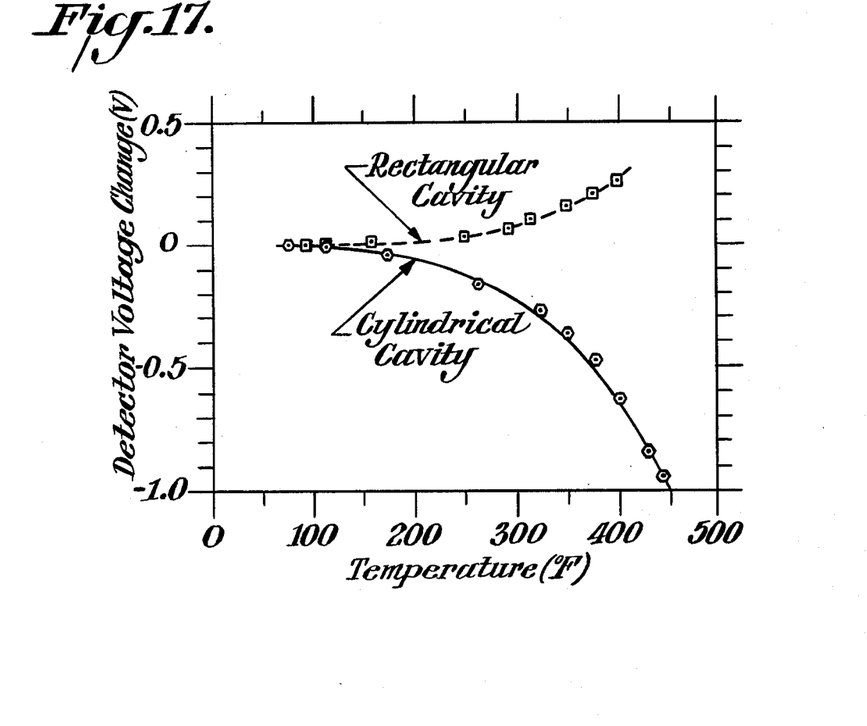
FIG. 17 is a graph of the change in the dc bias voltage of the Gunn flange attached to rectangular and cylindrical cavity systems as a function of the temperature of Antron ® dielectric material inserted into the cavity.
Figure 18:
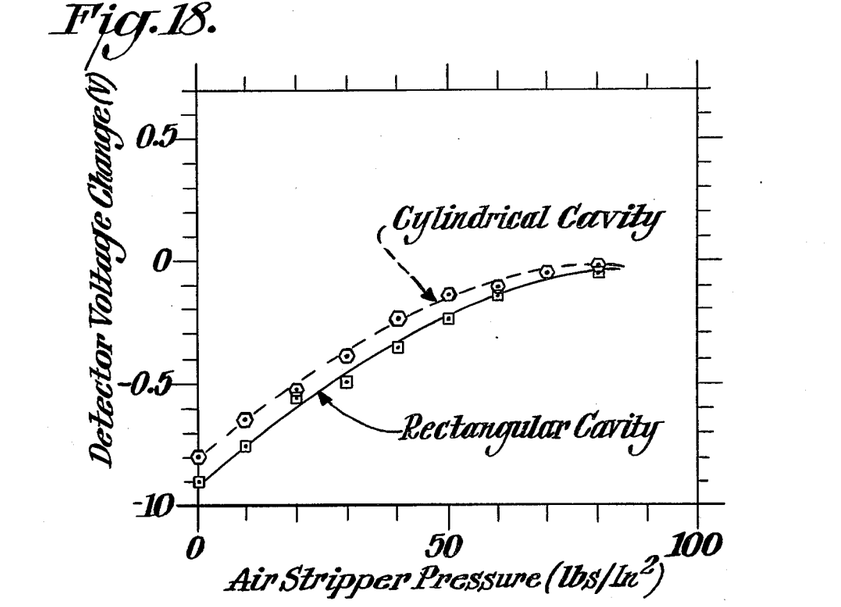
FIG. 18 is a graph of the change in the dc bias voltage of the Gunn flange attached to rectangular and cylindrical cavity systems as a function of the air stripper pressure which removed moisture from water dipped Kevlar ® material being inserted into the cavity.

In the examples given here, object size and dielectric constant are measured independently. However, any quantities related to these parameters such as object temperature or moisture content can also be measured using suitable calibrations. For example, FIG. 17 shows the changes in the dc bias voltage of the Gunn flange attached to a cavity as a function of the temperature of a ⅛ inch diameter Antron ®dielectric material inserted into the cavity. These data are obtained with sensor systems connected as shown in FIG. 11 with a 10 ohm series resistance 29, a 12 volt dc bias supply 27, and a dc voltmeter 33 as the output. Results for both the rectangular cavity system of FIG. 4 and the cylindrical cavity system of FIG. 8 are shown. Similar dc voltage change results, obtained as a function of the moisture content of Kevlar ®dielectric object material inserted into the cavity, are shown in FIG. 18 for these same two rectangular and cylindrical cavity sensor systems. Moisture was obtained by dipping the material into water until it absorbed water equal in weight to approximately 160 percent of the material's original dry weight. Water was removed by passing the Kevlar ®sample through a high pressure stream of dry air. When the air pressure applied to the air stream nozzle reached 80 pounds per square inch, more than 90 percent of the water was removed. This nozzle air pressure is indicated on the horizontal axis of FIG. 18. These FIGS. 17 and 18 data demonstrate the temperature and moisture measuring capabilities of the sensor system. For best agreement with the perturbation theory, the object size needs to be kept small so that $\epsilon' V_s/V_c$ is less than about $10^{-2}$. However, with calibration, parameter measurement with larger objects relative to cavity volume is possible.

Example Δf and ΔI Multiple Parameter Sensing System

Figure 19:
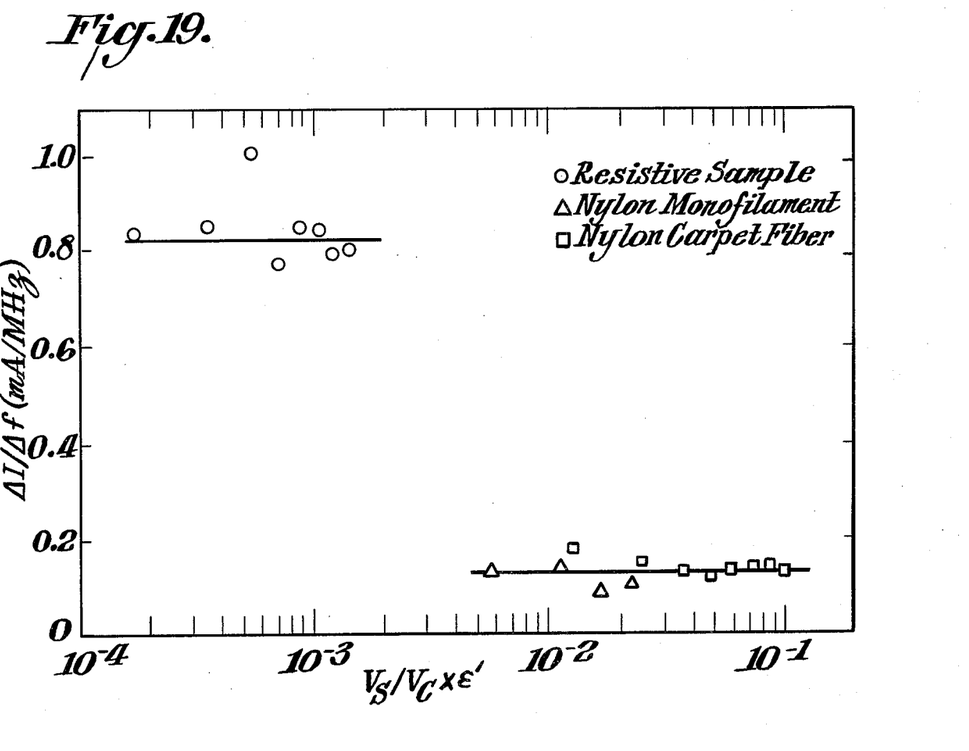
FIG. 19 is a graph of the ratio of current change to frequency change versus $(V_s/V_c)\epsilon'$ for objects inserted into the cylindrical cavity oscillating in the $TM_{010}$ mode.
Figure 20:
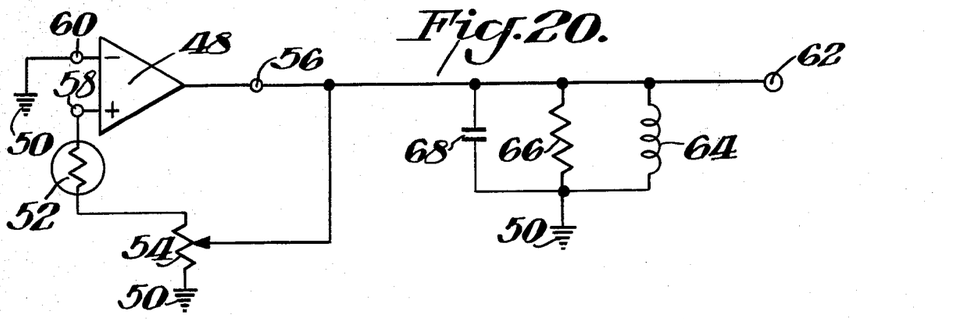
FIG. 20 is a representation of the resonant circuit sensor where the interaction of the sample and the oscillating waves occurs for waves in the form of an electric field and in the form of a magnetic field.

When the dc current change ΔI (or dc voltage change) as measured by 33 of device structures such as a Gunn flange 16 is monitored for an active cavity circuit such as shown in FIGS. 4 and 8, additional parameter sensing is possible. FIG. 19 shows the results of monitoring the ratio of ΔI/Δf for low loss nylon objects and high loss dielectric objects (resistive samples) loaded with a conducting material. As seen the lossy nature of the objects is sensed by a higher ΔI to Δf ratio. When this is combined with the Δf measurements described above, sample size and dielectric constant are measured and in addition, its high or low loss nature is sensed. Proper calibration allows actual values of sample resistivity to be measured in this way.

We claim:

1. Apparatus for the measurement of a plurality of physical properties of an object comprising:
   (a) resonant structure means which when properly energized responds with perturbed and unperturbed resonant oscillations with characteristics comprised of frequencies, amplitudes, phases, and polarizations;
   (b) means for providing a plurality of relative polarizations between the oscillations of the resonant structure means and the object measured;
   (c) energy source capable of energizing the oscillations of the resonant structure means at frequencies at which said structure means is resonant;
   (d) means for communicating energy between said energy source and the resonant structure means to energize the resonant oscillations;
   (e) means for communicating energy at a plurality of relative polarizations between said energized resonant structure means and the object whose properties are to be measured so that the resonant oscillations become perturbed;
   (f) detection means responsive to the characteristics of the resonant oscillations of the resonant structure means that is representative of the plurality of properties of the object measured.

2. Apparatus as in claim 1 in which the resonant oscillations are an electromagnetic field.

3. Apparatus as in claim 1 in which the resonant oscillations are an electrical field.

4. Apparatus as in claim 1 in which the resonant oscillations are a magnetic field.

5. Apparatus as in claim 1 in which the resonant oscillations are an acoustic wave.

6. Apparatus of claim 1 wherein the resonant structure is a cavity resonator.

7. Apparatus of claim 1 wherein the resonant structure is a circuit comprised of inductors and capacitors.

8. Apparatus as in claim 1 wherein the means for communicating energy between the energized resonant structure means and the object to be tested is done by incorporating the object as a part of the resonant structure means.

9. Apparatus as in claim 1 wherein the means for communicating energy between the energized resonant structure means and the object to be tested is located outside the resonant structure means.

10. Apparatus of claim 1 wherein the energy source also serves as the detection means.

11. Apparatus of claim 1 wherein the detection means is a frequency counter.

12. Apparatus of claim 1 wherein the detection means is an amplitude detector.

13. Apparatus of claim 1 wherein the detection means is a polarization detector.

14. Apparatus of claim 1 wherein the detection means is a phase detector.

15. Apparatus of claim 1 wherein the means for communicating energy between the energized resonant structure means and the object contains an amplifier.

16. Apparatus of claim 1 wherein the means for communicating energy between the energy source and the resonance structure contains an amplifier.

17. Apparatus of claim 1 wherein the medium through which the oscillations propagate is a gas.

18. Apparatus of claim 1 wherein the medium through which the oscillations propagate is a fluid.

19. Apparatus of claim 1 wherein the medium through which the oscillations propagate is a solid.

20. Apparatus of claim 2 wherein the medium through which the oscillations propagate is a vacuum.

21. Apparatus of claim 2 wherein means for communicating energy between the energy source and the resonant structure is a co-axial cable.

22. Apparatus of claim 3 wherein means for communicating energy between the energy source and the resonant structure is an electrical conductor.

23. Apparatus of claim 6 wherein the communication means are properly located in the cavity resonator.

24. Apparatus of claim 10 wherein the detector means is a voltmeter.

25. Apparatus of claim 10 wherein the detection means is an ammeter.

26. Apparatus for providing the measurement of a plurality of physical properties of an object in a given environment including:
   (a) microwave resonant structure means which, when properly energized, responds with unperturbed and unperturbed resonant, electromagnetic oscillations at characteristic frequencies, amplitudes, phases, and polarizations;

(b) means for providing a plurality of relative polarizations between the electromagnetic oscillations of the resonant structure means and the object measured;

(c) source of electromagnetic energy capable of energizing the resonant structure means at frequencies at which said structure means is resonant;

(d) means for communicating electromagnetic energy from said energy source to excite resonant oscillations in the resonant structure means;

(e) means for communicating electromagnetic energy at a plurality of polarizations between said energized resonant structure means and the object whose properties are to be measured so that the resonant oscillations become perturbed;

(f) detection means responsive to the perturbation of the frequencies, amplitudes, phases, and polarizations of the resonant, electromagnetic oscillations of the resonant structure means that is characteristic of a plurality of properties of the object measured.

27. Apparatus of claim 26 wherein the energy source is a Gunn device.

28. Apparatus of claim 26 wherein the energy source is an IMPATT device.

29. Apparatus of claim 26 wherein means for communicating energy between the energy source and the resonant structure is a waveguide.

30. Apparatus of claim 26 wherein the detection means and the energy source are both comprised of a single Gunn device.

31. Apparatus of claim 26 wherein the energy source is a Sharpless flange containing an active microwave emitting device.

32. Apparatus of claim 26 wherein the resonant structure is a rectangular microwave cavity capable of oscillating in the $TE_{101}$ mode.

33. Apparatus of claim 26 wherein the resonant structure is a cylindrical microwave cavity capable of oscillating in the $TM_{010}$ and $TE_{112}$ modes.

34. A method for the measurement of a plurality of physical properties of an object which comprises:

(a) energizing a resonant structure means whereby it responds with perturbed and unperturbed resonant oscillations;

(b) polarizing the oscillations of the resonant structure means relative to the object whose properties are to be measured;

(c) placing the object whose physical properties are to be measured in a position which is relative to the polarized oscillations of the resonant structure means whereby the resonant oscillations are perturbed;

(d) measuring the perturbed characteristics of the oscillations which are comprised of frequencies, amplitudes, phases, and polarizations whereby the physical properties of the object are determined.

* * * * *